(12) United States Patent
Iyer et al.

(10) Patent No.: US 7,839,620 B2
(45) Date of Patent: Nov. 23, 2010

(54) FILTERED FEEDTHROUGH ASSEMBLIES FOR IMPLANTABLE DEVICES AND METHODS OF MANUFACTURE

(75) Inventors: Rajesh V. Iyer, Eden Prairie, MN (US); Thomas P. Miltich, Otsego, MN (US)

(73) Assignee: Medtronic, Inc., Minneapolis, MN (US)

( * ) Notice: Subject to any disclaimer, the term of this patent is extended or adjusted under 35 U.S.C. 154(b) by 534 days.

(21) Appl. No.: 11/858,498

(22) Filed: Sep. 20, 2007

(65) Prior Publication Data
US 2009/0080140 A1 Mar. 26, 2009

(51) Int. Cl.
*H01G 4/35* (2006.01)

(52) U.S. Cl. ........................ 361/302; 361/305; 361/307; 361/311; 361/313; 607/5; 607/36; 607/7

(58) Field of Classification Search ................. 361/302, 361/303–305, 311–313, 307; 429/885; 607/5, 607/9, 36, 37
See application file for complete search history.

(56) References Cited

U.S. PATENT DOCUMENTS

| | | | |
|---|---|---|---|
| 5,032,692 A | 7/1991 | Devolder | |
| 5,242,097 A | 9/1993 | Socha | |
| 5,867,361 A | 2/1999 | Wolf et al. | |
| 5,870,272 A * | 2/1999 | Seifried et al. | 361/302 |
| 5,905,627 A * | 5/1999 | Brendel et al. | 361/302 |
| 6,008,980 A | 12/1999 | Stevenson et al. | |
| 6,031,710 A | 2/2000 | Wolf et al. | |
| 6,275,369 B1 | 8/2001 | Stevenson et al. | |
| 6,414,835 B1 * | 7/2002 | Wolf et al. | 361/302 |
| 6,459,935 B1 * | 10/2002 | Piersma | 607/37 |
| 6,490,148 B1 * | 12/2002 | Allen et al. | 361/302 |
| 6,529,103 B1 * | 3/2003 | Brendel et al. | 333/182 |
| 6,566,978 B2 * | 5/2003 | Stevenson et al. | 333/182 |
| 6,768,629 B1 | 7/2004 | Allen et al. | |
| 7,012,192 B2 * | 3/2006 | Stevenson et al. | 174/538 |
| 7,038,900 B2 | 5/2006 | Stevenson et al. | |
| 7,391,601 B1 * | 6/2008 | Imani | 361/302 |
| 2003/0123215 A1 | 7/2003 | Allen et al. | |
| 2005/0247475 A1 | 11/2005 | Stevenson et al. | |
| 2007/0053137 A1 | 3/2007 | Fu et al. | |
| 2007/0179554 A1 | 8/2007 | Iyer et al. | |

OTHER PUBLICATIONS

International Search Report, PCT/US2008/075769, Dec. 18, 2008, 7 Pages.

* cited by examiner

*Primary Examiner*—Nguyen T Ha

(57) ABSTRACT

A solder joint between a capacitive element and a ferrule of a filtered feedthrough assembly for an implantable medical device is formed from a solder pre-form mounted on a portion of an external surface of the capacitive element, which portion of the external surface may be overlaid with a layer including a noble metal. Another solder joint may be formed between the capacitive member and each feedthrough pin; and, for an assembly including a plurality of feedthrough pins, each of the other solder joints may be formed from a solder pre-form mounted onto the external surface of the capacitive element by inserting each pin through a corresponding ring of a plurality of rings connected together to form the solder pre-form.

16 Claims, 6 Drawing Sheets

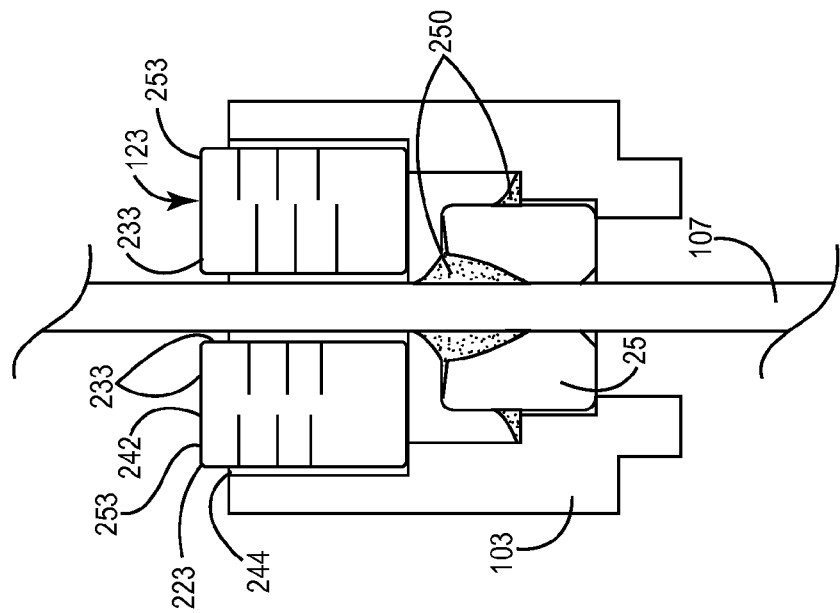
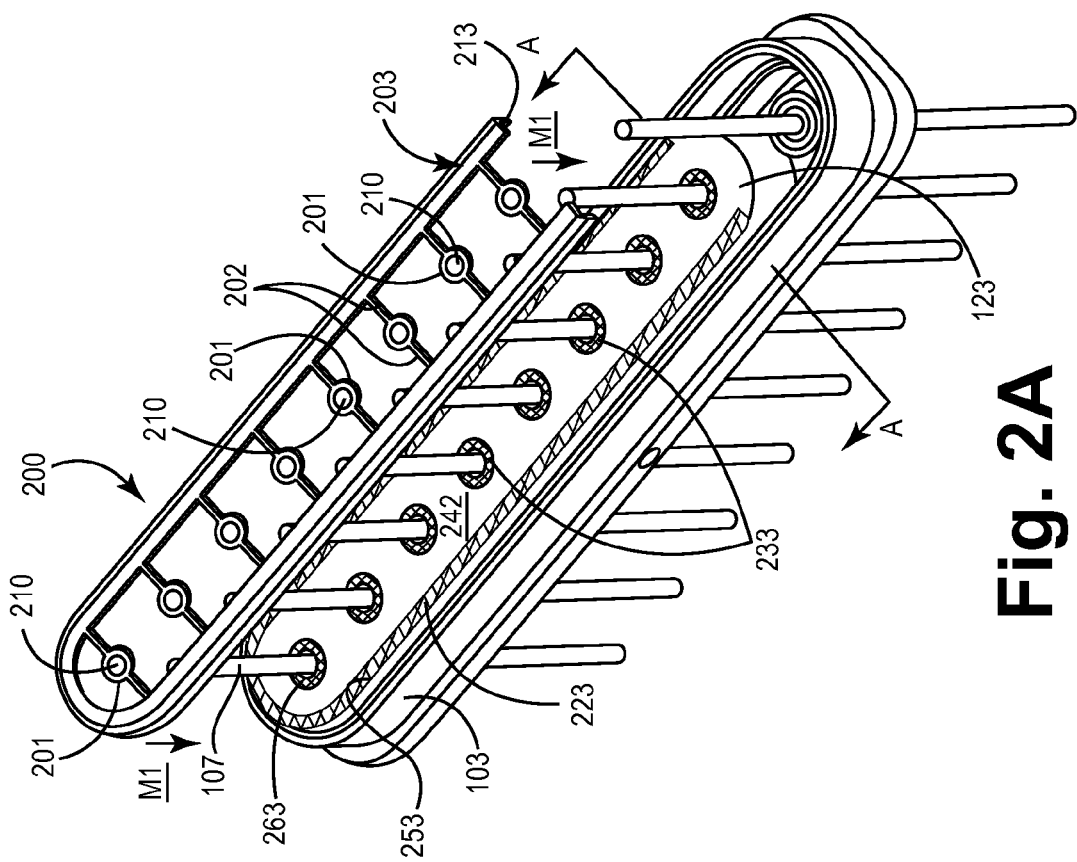

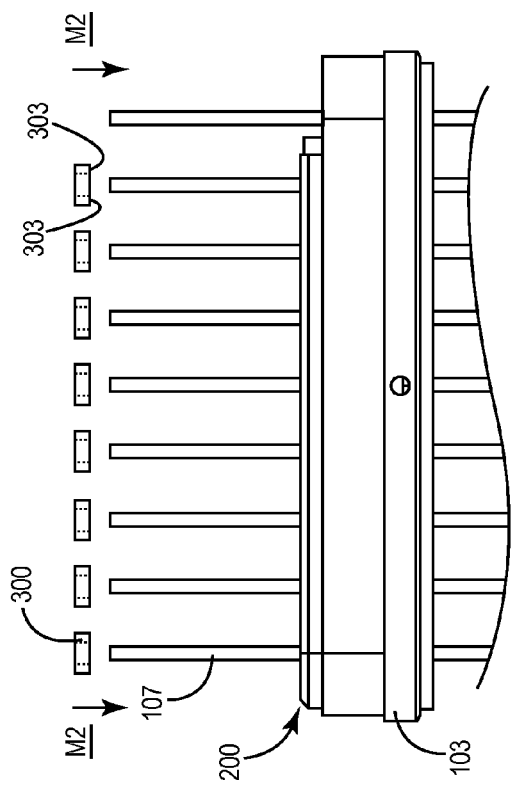
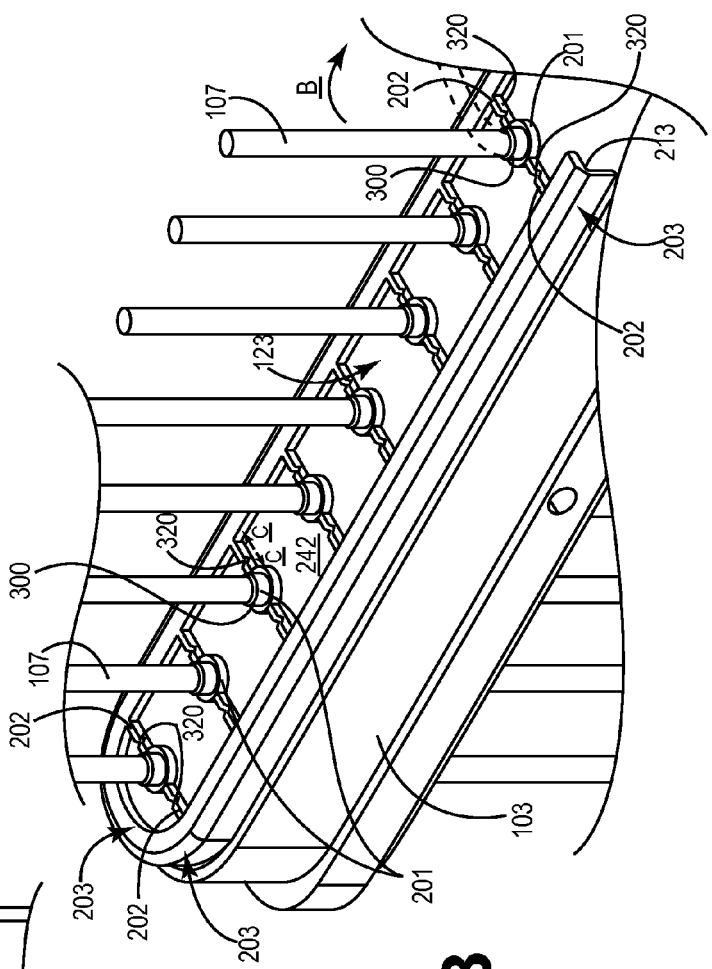
Fig. 3A
Fig. 3B

FILTERED FEEDTHROUGH ASSEMBLIES FOR IMPLANTABLE DEVICES AND METHODS OF MANUFACTURE

TECHNICAL FIELD

The present invention pertains to feedthrough assemblies for implantable medical devices and more particularly to incorporation of capacitive elements therein.

BACKGROUND

Implantable medical devices (IMDs), for example, cardiac pacemakers, defibrillators, neurostimulators and drug pumps, which include electronic circuitry and battery elements, require a housing to contain and hermetically seal these elements within a body of a patient. Many of these IMDs include one or more electrical feedthrough assemblies to provide electrical connection between the elements contained within the housing and components of the IMD external to the housing, for example, sensors and/or electrodes and/or lead wires mounted on an exterior surface, or electrical contacts housed within a connector module, which is mounted on the housing, to provide coupling for lead wires.

A feedthrough assembly for an IMD can be unipolar or multipolar; a unipolar feedthrough assembly includes a single feedthrough member, or pin that extends from an interior to an exterior of the housing through a ferrule, while a multipolar feedthrough assembly includes a plurality of such feedthrough pins extending through a single ferrule. In each type of assembly, the feedthrough pin(s) is/are electrically isolated from the ferrule, and, in the case of the multipolar assembly, from one another, by an insulator element, for example, glass or ceramic, that is mounted within the ferrule and surrounds the feedthrough pin(s). The insulator element is hermetically sealed to the ferrule and to the feedthrough pin(s), typically, by a braze joint.

To reduce the effects of stray electromagnetic interference (EMI) signals that may be collected by lead wires electrically coupled to the feedthrough pins, it is known to incorporate, within feedthrough assemblies, capacitive elements for high frequency filtering. A filtered feedthrough assembly may be formed by mounting the capacitive element within the ferrule after sealing the insulator element to the ferrule and the feedthrough pin(s); the capacitive element typically includes an insulative base, for example, a ceramic monolith, in which electrode plates are embedded, otherwise known as a discoidal-type capacitor. A first set of the electrode plates are electrically coupled to a conductive layer overlaying an inner surface of the capacitor, and a second set of the electrode plates are electrically coupled to another conductive layer overlaying an outer surface of the capacitor.

After mounting the capacitor within the ferrule and around the pin(s), an electrical coupling, or joint, is formed between the first set of electrode plates and the pin(s), and between the second set of electrode plates and the ferrule. This coupling is typically formed by a conductive material extending between the inner surface of the capacitor and each pin, and between the outer surface of the capacitor and the ferrule. If the conductive material is solder, solder pre-forms may be mounted onto an exposed surface of the mounted capacitive element; upon heating the pre-forms, those pre-forms mounted in proximity to each pin flow between the inner surface of the capacitive element and each pin to form the electrical coupling therebetween, and the other pre-form, which is mounted in proximity to the ferrule, flows between the ferrule and the outer surface of the capacitive element to form the electrical coupling therebetween. The use of solder pre-forms can help to improve process consistency and efficiency in manufacturing relatively large quantities of feedthrough assemblies; yet there is still a need for feedthrough assembly features that can further improve consistency and efficiency in manufacturing.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 2A is a perspective view of a feedthrough assembly in the process of being assembled, according to some embodiments of the present invention.

FIG. 2B is a cross-section view of a portion the assembly shown in FIG. 2A, through section line A-A of FIG. 2A, according to some embodiments of the present invention.

FIG. 3A is an elevation view of a feedthrough assembly in the process of being assembled, according to some alternate embodiments of the present invention.

FIG. 3B is a perspective view of a portion of the assembly shown in FIG. 3A, upon completion of an assembly step illustrated by FIG. 3A, according to some embodiments.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

One embodiment of the present invention involves a novel method of attaching at least one or more capacitors in a filtered feedthrough using solder pre-forms. This type of capacitor attachment eliminates the need for dispensing conductive epoxy or conductive polyimide to make the connection between the capacitor and the feedthrough pin and between the capacitor and the ferrule. The process is simplified, since this type of capacitor attachment also eliminates the need to seal the bottom of the capacitor with non-conductive sealant (e.g. epoxy) that is used to contain the conductive epoxy in the annular space within the capacitor.

Figure 1B:
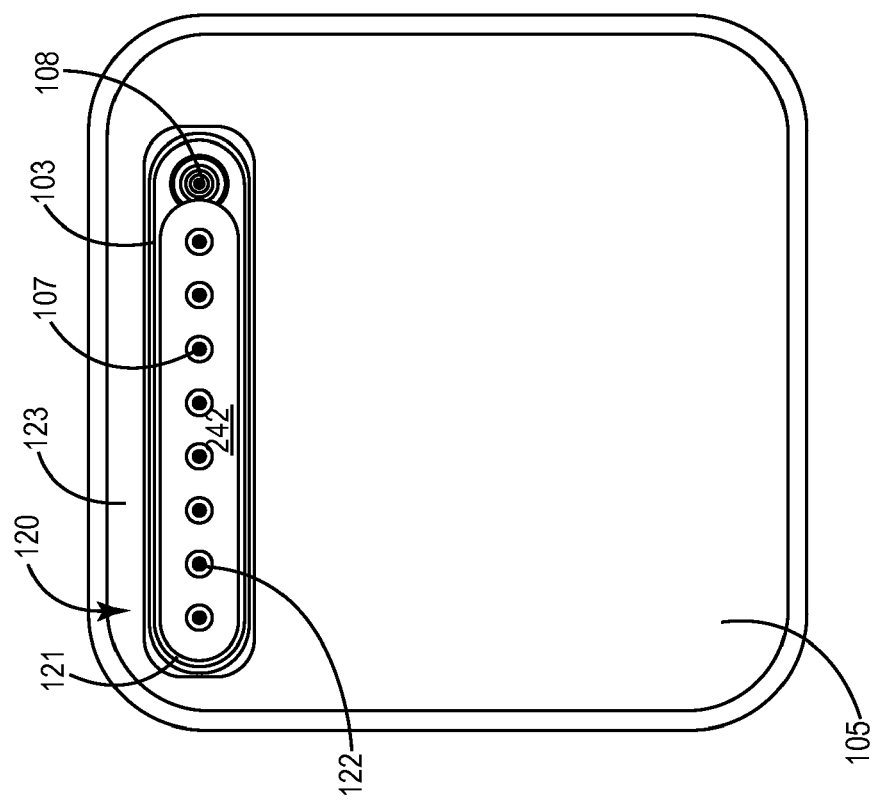
FIG. 1B is a plan view of a portion of the IMD shown in FIG. 1A that includes a multi-polar filtered feedthrough assembly, according to some embodiments of the present invention.
Figure 1A:
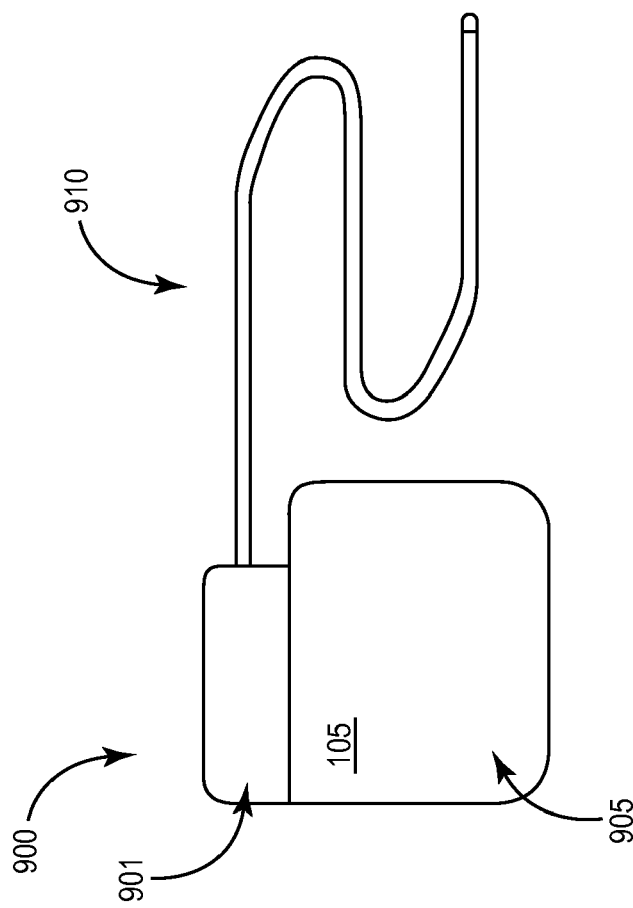
FIG. 1A is a plan view of an IMD system, according to exemplary embodiments of the present invention.

FIG. 1A is a plan view of an IMD system, according to exemplary embodiments of the present invention; and FIG. 1B is a plan view of a portion of the IMD shown in FIG. 1A. FIG. 1A illustrates the system including a stimulation source, or device 900, coupled to a medical electrical lead 910 via coupling of a connector end (not shown) of lead 910 to electrical contacts (not shown) within a header block 901 of device 900. FIG. 1A further illustrates device 900 including a can, or housing 905 to which header block 901 is attached. Those skilled in the art will appreciate that hermetically sealed feedthrough elements, or pins, extend through a sidewall 105 of housing 905 in order to electrically couple the contacts, within header block 901, to electronic circuitry enclosed within housing 905. FIG. 1B shows an interior side of sidewall 105 of housing 905 to which a multi-polar filtered feedthrough assembly 120, according to some embodiments of the present invention, is attached; feedthrough assembly 120 includes eight filtered feedthrough pins 107 and a single unfiltered feedthrough pin 108 extending within a ferrule 103, which is joined to housing sidewall 105, for example, via laser welding. Suitable materials for feedthrough members 107, 108 and ferrule 103 include, without limitation, titanium, niobium, platinum, molybdenum, zirconium and tantalum. FIG. 1B further illustrates a capacitive element 123, which surrounds filtered feedthrough pins 107 to provide for the filtering thereof, electrically coupled, via a conductive material 121, to ferrule 103 and, via a conductive material 122, to pins 107. Those skilled in the art will understand that an insulator element 25 (FIG. 2B), which is hermetically sealed around each pin 107, 108 and within ferrule 103, for example, by braze joints 250, underlies capacitive element 123 of feedthrough assembly 120 seen in FIG. 1B.

According to preferred embodiments of the present invention, conductive materials 121 and 122 are both solder materials, which have been re-flowed from one or more solder pre-forms mounted over a surface 242 of capacitive element 123. FIG. 2A is a perspective view of feedthrough assembly 120, in-process, wherein a solder pre-form 200 is positioned for mounting, per arrow M1, over surface 242 of capacitive element 123; and FIG. 2B is a cross-section view of a portion assembly 120, through section line A-A of FIG. 2A. FIG. 2A illustrates solder pre-form 200 including a plurality of rings 201, each having an inner diameter 210 to fit around the corresponding feedthrough pin 107, and an outer member 203 surrounding rings 201; rings 201 are connected to one another via a connection to outer member 203 by stringers 202 that extend from either side of each ring 201 to outer member 203. It should be understood that an entirety of pre-form 200 including rings 201, stringers 202 and outer member 203, are formed of solder material, suitable examples of which include, without limitation, both lead-based and lead-free solder alloys, which may be flux cored or fluxless pre-forms of the following alloys and combinations thereof: tin-based, gold-based, and indium-based. According to the illustrated embodiment, outer member 203 of pre-form 200 includes a bend 213 for conforming around an edge 223 of capacitive element 123, for example as is illustrated in FIG. 3B.

FIGS. 2A-B further illustrate surface 242 including portions 233 and 253, which are metalized, that is, overlaid with a layer including a noble metal, for example, gold. According to an exemplary embodiment, metalized portions 233, 253 are formed by sputtering, in series, first titanium, then nickel, and then gold onto surface 242. Portion 253 underlies outer member 203 of solder pre-form 200, and each of portions 233 underlie a corresponding ring 201, when pre-form is mounted on surface 242, for example as illustrated in FIG. 3B; the solder will more readily wet to portions 233, 253, which may provide a particular advantage in enhancing a flow of fluxless solder materials. Other portions of surface 242, which underlie stringers 202, are not metalized. According to the illustrated embodiment, when pre-form 200 is heated, for example, to a temperature in the range of approximately 150° C. to approximately 550° C. (depending on the particular solder alloy), for example, by placing assembly 410 in a re-flow oven, under vacuum and/or in an inert atmosphere, rings 201 and outer member 203 will wet to metalized portions 233 and 253, respectively, while the solder material of stringers 202 will bead up and roll over, for example, per arrows C (FIG. 3B), the underlying non-metalized portions of surface 242, without adhering thereto, toward either, or both of metalized portions 233, 253, where the material of stringers 202 will coalesce with the solder material of either, or both of rings 202 and outer member 203, respectively. Thus, when solder pre-form 200 is heated, a first portion of the solder material of pre-form 200 will flow toward each pin 107 to form a joint between each inner surface 233 of capacitive element 123 and the corresponding pin 107, and the remaining portion of the solder material of pre-form 200 will flow toward ferrule 103 to form a joint between an outer surface 244 of capacitive element 123 and ferrule 103. Additional, optional, features of pre-form 200 will be described in conjunction with FIG. 3B.

FIG. 3A is an elevation view of feedthrough assembly 120, according to an alternate embodiment, wherein strain relief members 300 are to be incorporated. FIG. 3A illustrates each strain relief member 300 positioned for mounting around a corresponding feedthrough pin 107, per arrow M2; and FIG. 3B is a perspective view of a portion of the assembly wherein each member 300 is mounted over a corresponding ring 201 of the mounted solder pre-form 200. FIG. 3B illustrates strain relief members 300, for example, alumina washers, being mounted around pins 107 prior to heating solder pre-form 200 to form the aforementioned joints between capacitive element 123 and ferrule 103 and between capacitive element 123 and pins 107; after these joints are formed, strain relief members 300 serve to protect the joint between each pin 107 and capacitive member 123 when pins 107 are bent, for example, via arrow B of FIG. 3B, in order to electrically connect pins 107, for example, via wire bonding, parallel gap welding, or laser welding, to circuitry contained within device housing 905 (FIG. 1A). According to some preferred embodiments of the present invention, which incorporate strain relief members 300, a surface 303 of each member 300 that interfaces with the corresponding ring 201 of solder pre-form 200 is metalized, or overlaid with a layer including a noble metal, similar to portions 223 and 233 of capacitive element 123, as previously described in conjunction with FIGS. 2A-B, in order that re-flowed solder material of pre-form 200 will wet and adhere to surfaces 303.

FIG. 3B further illustrates each stringer 202 of solder pre-form 200 including a discontinuity 320, according to some preferred embodiments. Discontinuities 320 may be formed, for example, via stamping, scribing or chemically etching, grooves or notches in surfaces of stringers 202, either during the process of forming pre-form 200 or after pre-form 200 is formed, either prior to or after mounting onto surface 242 of capacitive element 123. According to the illustrated embodiment, discontinuities 320 are located such that when pre-form is heated, the solder material of each stringer 202 preferentially flows apart from the corresponding discontinuity 320, per arrows C; thus, incorporation of discontinuities 320 can provide extra assurance, in addition to the absence of metallization on surface 242 underlying stringers 202 (previously described), that the solder material of stringers 202 will either coalesce at the joints between pins 107 and capacitive element 123 or at the joint between ferrule 103 and capacitive element 123 without leaving a pathway for an electrical short between the joints.

Figure 4B:
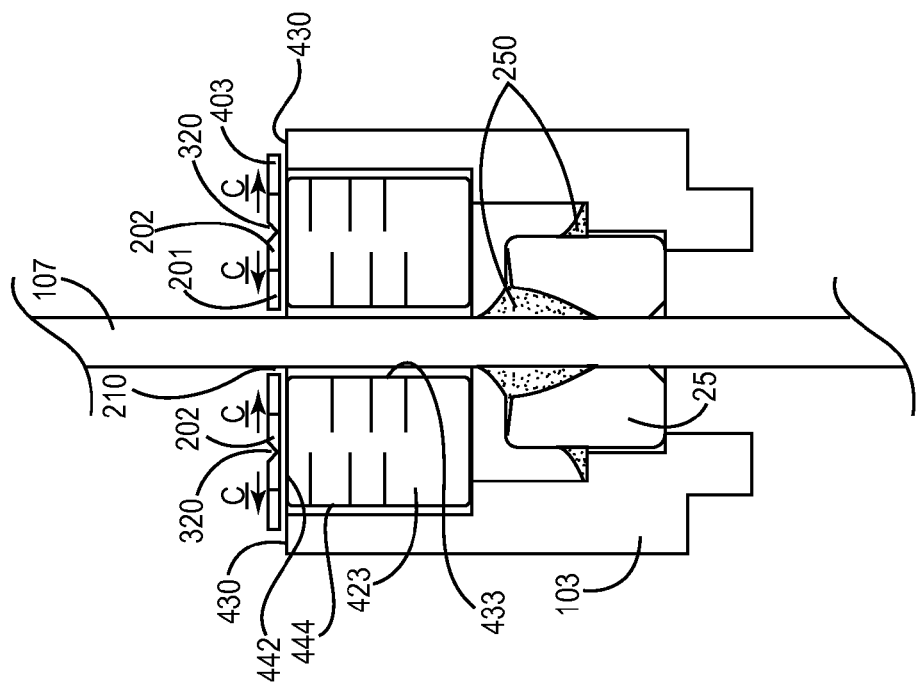
FIG. 4B is a cross-section view of a partially assembled feedthrough assembly including the solder pre-form shown in FIG. 4A.
Figure 4A:
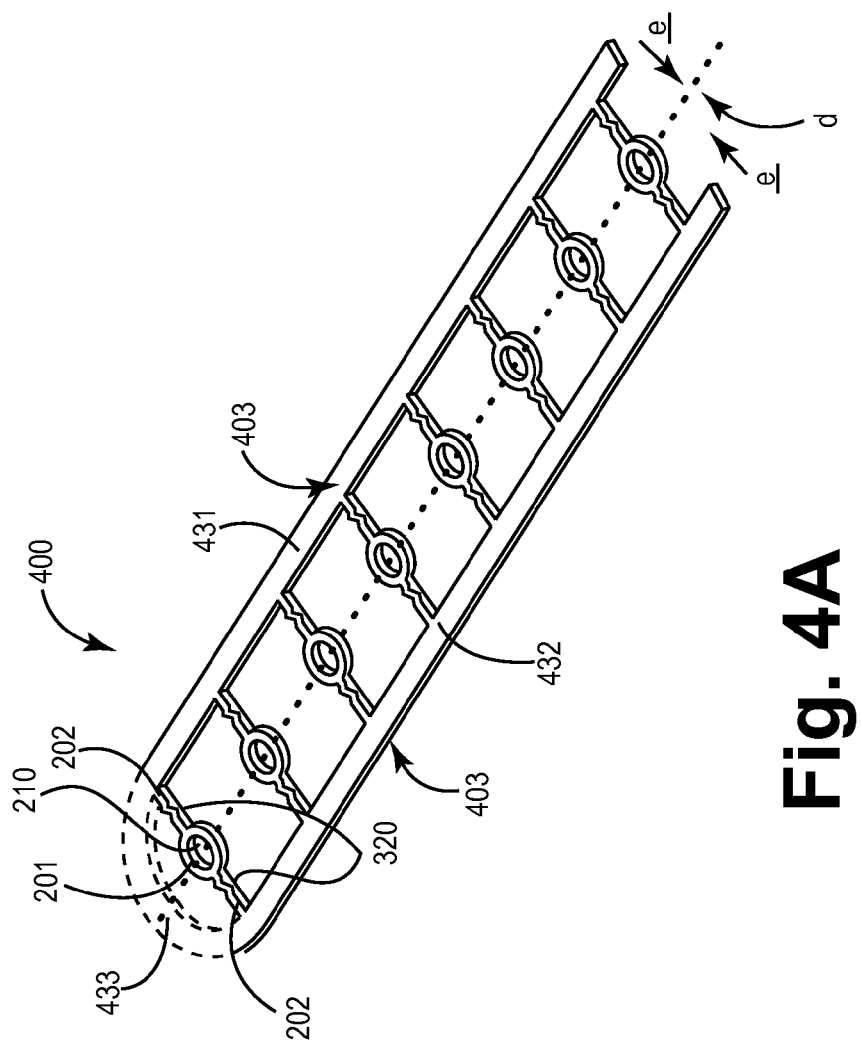
FIG. 4A is a perspective view of a solder pre-form, according to some embodiments of the present invention.

FIG. 4A is a plan view of a solder pre-form 400, according to some other embodiments of the present invention; and FIG. 4B is a cross-section view of a partially assembled feedthrough assembly including pre-form 400. FIG. 4A illustrates solder pre-form 400 including rings 201 and an outer member 403 extending alongside rings 201; rings 201 are connected to one another via a connection to first and second parts 431, 432 of outer member 403 by stringers 202 that extend from either side of each ring 201 to outer member 403. An optional third part 433 of outer member is shown with dashed lines and connects first part 431 to second part 432. Like pre-form 200, described above, it should be understood that an entirety of pre-form 400 including rings 201, stringers 202 and outer member 403, are formed of any of the suitable solder materials described above. FIG. 4A further illustrates each stringer 202 of pre-form 400 including the optional discontinuities 320, as previously described for pre-form 200, and FIG. 4B illustrates in cross-section, the flow of the solder material of stringers 202, per arrows C, as previously described for pre-form 200.

Figure 5:
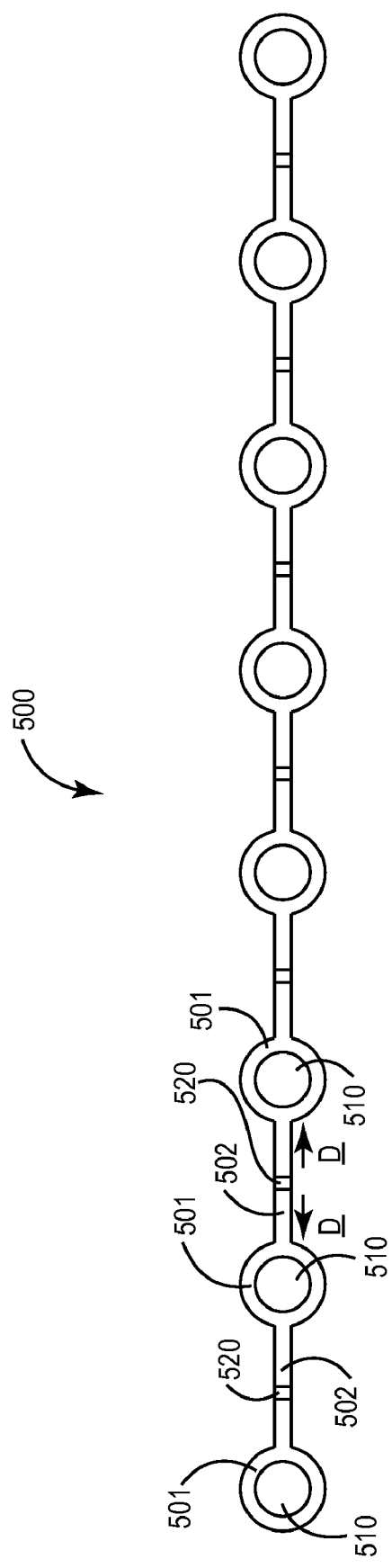
FIG. 5 is a plan view of a solder pre-form, according to some alternate embodiments of the present invention.

With further reference to FIG. 4B, it may be appreciated that a capacitive element 423 of the feedthrough assembly fits within ferrule 103 such that an external surface 442 thereof is approximately flush with an edge 430 of ferrule 103. Although outer member 403 of solder pre-form 400 is shown having a rectangular cross-section and spanning across a gap between an outer surface 444 of capacitive element 423 and edge 430 of ferrule 103, it should be appreciated that the invention is not so limited and the cross-section of outer member 403 may be any other geometry, and may further be sized to, at least partially, fit within the gap between capacitive element 423 and ferrule 103, when pre-form 400 is mounted on surface 442 of capacitive element 423, according to alternate embodiments. Furthermore, alternate embodiments of the present invention may employ more than one solder pre-form, for example, either one or two 'outer' pre-forms, to form the electrical coupling between capacitive element 123/423 and ferrule 103, and at least one 'inner' pre-form to form the electrical coupling between each filtered feedthrough pin 107 and capacitive element 123/423. An exemplary embodiment of the at least one 'inner' pre-form is shown in FIG. 5. Alternatively, with reference to FIG. 4A, pre-form 400 may be divided into two portions, for example, along dotted line d, such that each feedthrough pin 107 is inserted into the corresponding ring 201 by bringing the two portions of pre-form together, per arrows e, around pins 107.

FIG. 5 is a plan view of a solder pre-form 500, according to yet further embodiments of the present invention. FIG. 5 illustrates pre-form 500 including a plurality of solder rings 501, each having an inner diameter 510 to fit around a corresponding feedthrough pin, for example pins 107; rings 501 are connected together by solder stringers 502 extending between adjacent rings 501. FIG. 5 further illustrates each solder stringer 502 including an optional discontinuity 520, similar to discontinuities 320 previously described. According to the illustrated embodiment, pre-form 500 is mounted onto a surface of a capacitive element in a partially assembled feedthrough assembly, for example, element 123 or 423, such that each ring 501 surrounds a corresponding feedthrough pin extending though the capacitive element; another one or more of 'outer' solder pre-forms are mounted on the capacitive element in proximity to a ferrule in which capacitive element is mounted, for example, ferrule 103. When mounted pre-form 500, along with the mounted outer pre-form(s), is heated, the solder material of stringers 502 preferentially flows, for example, per arrows D, to coalesce with the solder material of rings 501 and form the electrical couplings between each pin and the capacitive element of the feedthrough assembly.

According to some exemplary embodiments of the present invention: an average wall thickness of pre-forms 200, 400, 500 ranges from approximately 0.003 inch to approximately 0.007 inch; rings 201, 501 have inner diameters ranging from approximately 0.015 inch to approximately 0.022 inch, and outer diameters ranging from approximately 0.025 inch to approximately 0.032 inch; a length of each stringer 202, between rings 201 and outer member 203/403 of pre-forms 200, 400, ranges between approximately 0.020 inch and approximately 0.030 inch; and a length of each stringer 502, between each adjacent ring 501 of pre-form 500, ranges between approximately 0.040 inch and approximately 0.055 inch. Of course any solder pre-form dimensions that are suitable for particular feedthrough assembly designs may be employed by embodiments of the present invention.

Figure 6:
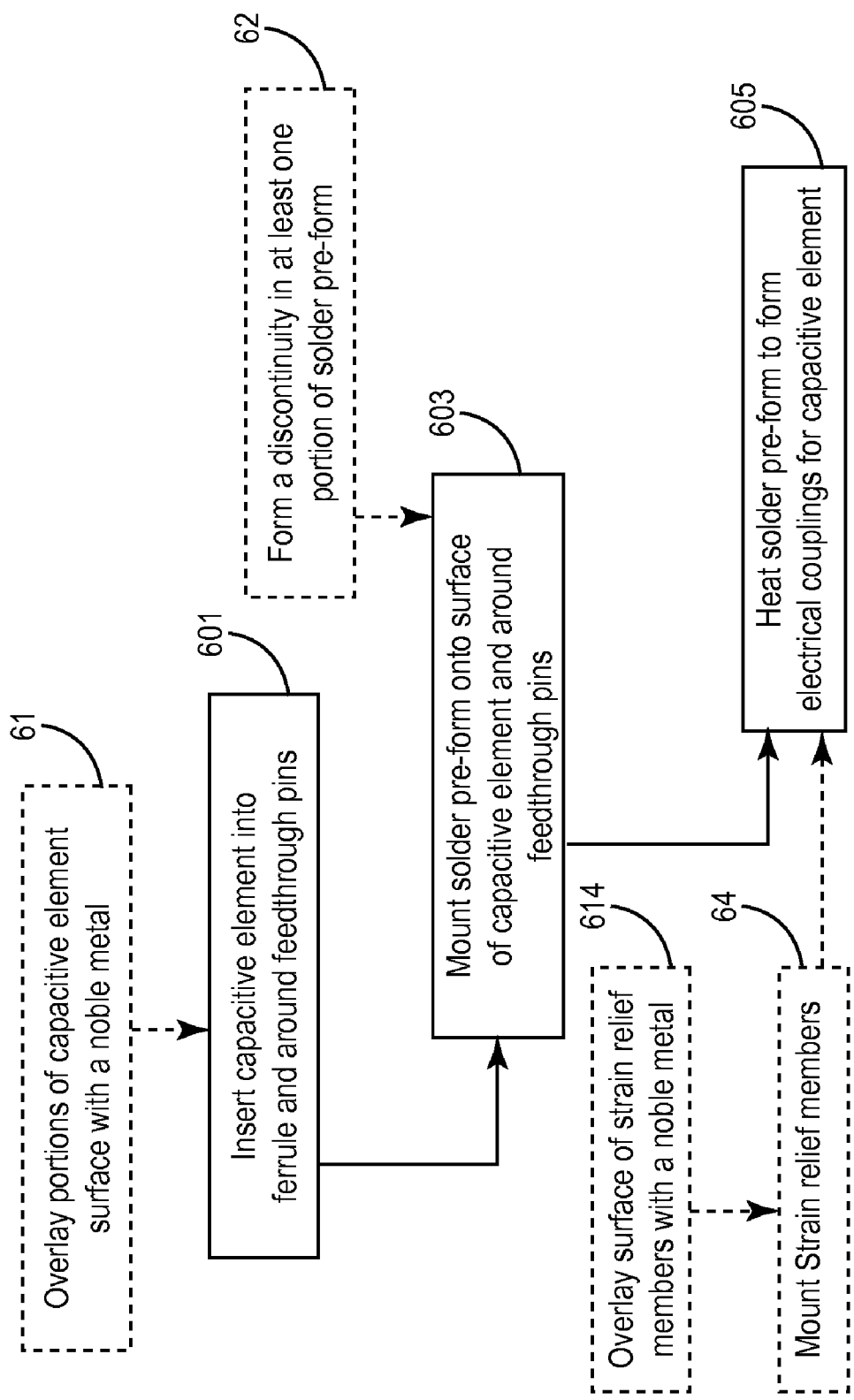
FIG. 6 is a flow chart outlining some methods of the present invention.

FIG. 6 is a flow chart outlining some methods of the present invention which have been described above; dashed lines indicate optional steps. FIG. 6 illustrates an initial step 601 wherein a capacitive element (i.e. element 123 or 423) is inserted into a ferrule (i.e. 103) and around feedthrough pins (i.e. pins 107), for example, as is illustrated in FIG. 2A; an optional step 61 is shown preceding step 601, wherein portions of the capacitive element (i.e. portions 223, 233 of element 123) are overlaid with a noble metal. Next, according to a step 603, a solder pre-form (i.e. pre-form 200, 400, or 500) is mounted onto a surface of the capacitive element and around the feedthrough pins, and then, per a step 605, the pre-form is heated to re-flow and form electrical couplings for the capacitive element. As previously described, one or more solder pre-forms may be employed by a single feedthrough assembly; according to preferred embodiments, a single pre-form is mounted for forming the couplings between the feedthrough pins and the capacitive element, and between the ferrule and the capacitive element, simultaneously. Alternately, more than one pre-form can be employed for either sequential or simultaneous forming of the various electrical couplings for the capacitive element. An optional step 62, in which a discontinuity (i.e. 320 or 520) is formed in at least one portion the pre-form, for example, in one or more stringers (i.e. stringers 202 or 502), is shown preceding step 603; however, it should be noted that, alternatively, this optional step 62 may follow step 603 such that each discontinuity is formed in the pre-form, after the pre-form is mounted, and before step 605 wherein the pre-form is heated.

FIG. 6 further illustrates an optional step 64, wherein strain relief members (i.e. members 300) are mounted around each feedthrough pin that extends through the capacitive element, for example as illustrated in FIGS. 3A-B. Optional step 64 may be preceded by another optional step 614 in which a surface of each strain relief member (i.e. surface 303) is overlaid with a noble metal, for example, via sputtering, wherein the overlaid surface of each mounted strain relief member interfaces with the solder pre-form.

The present invention allows fluxless or fluxed solder could be used. Sealing under the capacitor could be avoided since the solder would not fill the entire volume inside the capacitor inner diameter (ID). Capacitor ID to the pin and the outer diameter (OD) to the ferrule can be attached at the same time along with the strain relief washer. A number of process operations and piece parts are reduced with the use of this method. A metallurgical bond is achieved between the pin to the capacitor ID and between the capacitor OD to the ferrule formed using solder. This bond is far superior in electrical performance compared to epoxy or polyimide.

In the foregoing detailed description, the invention has been described with reference to specific embodiments. However, it may be appreciated that various modifications and changes can be made without departing from the scope of the invention as set forth in the appended claims. For example any combination of integrated solder pre-form configurations described herein, having any suitable cross-sectional geometry, with any combination of interfacing metalized surfaces of either capacitive elements or strain relief members described herein may be employed by embodiments of the present invention.

The invention claimed is:

1. A filtered feedthrough assembly for an implantable medical device, the assembly comprising:
   a ferrule;
   a feedthrough pin extending within the ferrule;
   a capacitive element located within the ferrule, the capacitive element including a bore, through which the pin extends, and an external surface extending laterally outward from an opening of the bore; and
   a first solder joint coupling the capacitive element to the ferrule;
   wherein the external surface of the capacitive element includes a first portion adjacent to the first solder joint, the first portion being overlaid with a layer comprising a noble metal.

2. The assembly of claim 1, further comprising a non-conductive strain-relief member mounted on the external surface of the capacitive element and surrounding the pin.

3. The assembly of claim 1, further comprising:
   a second solder joint coupling the capacitive element to the pin; and
   wherein the external surface of the capacitive element further includes a second portion adjacent the second solder joint, the second portion being overlaid with a layer comprising a noble metal.

4. The assembly of claim 3, further comprising a non-conductive strain-relief member mounted over the second solder joint and surrounding the pin.

5. A solder pre-form used in manufacturing a feedthrough assembly for an implantable medical device, the solder pre-form comprising a plurality of rings connected together, each ring of the plurality of rings having an inner diameter sized to fit around a feedthrough pin of the feedthrough assembly.

6. The solder pre-form of claim 5, wherein the plurality of rings are connected together by a stringer extending between adjacent rings of the plurality of rings.

7. The solder pre-form of claim 6, wherein each stringer includes a discontinuity.

8. The solder pre-form of claim 5, further comprising an outer member extending alongside the plurality of rings and being connected to at least one ring of the plurality of rings.

9. The solder pre-form of claim 5, further comprising an outer member extending alongside the plurality of rings; and wherein the plurality of rings are connected together by the outer member, and at least one stringer extends between each ring of the plurality of rings and the outer member.

10. The solder pre-form of claim 9, wherein each of the at least one stringers includes a discontinuity.

11. The solder pre-form of claim 5, further comprising an outer member extending alongside the plurality of rings and being connected to at least one ring of the plurality of rings; wherein the outer member includes a bend for conforming around an edge of a capacitive element of the feedthrough assembly.

12. An implantable medical device comprising a housing and a filtered feedthrough assembly extending therethrough, the filtered feedthrough assembly comprising:
   a ferrule coupled to the housing of the device;
   a feedthrough pin extending within the ferrule;
   a capacitive element located within the ferrule, the capacitive element including a bore, through which the pin extends, and an external surface extending laterally outward from an opening of the bore; and
   a first solder joint coupling the capacitive element to the ferrule;
   wherein the external surface of the capacitive element includes a first portion adjacent to the first solder joint, the first portion being overlaid with a layer comprising a noble metal.

13. The device of claim 12, wherein the feedthrough assembly further comprises a non-conductive strain-relief member mounted on the external surface of the capacitive element and surrounding the pin.

14. The device of claim 12, wherein the feedthrough assembly further comprises:
   a second solder joint coupling the capacitive element to the pin; and
   wherein the external surface of the capacitive element further includes a second portion adjacent the second solder joint, the second portion being overlaid with a layer comprising a noble metal.

15. The device of claim 14, wherein the feedthrough assembly further comprises a non-conductive strain-relief member mounted over the second solder joint and surrounding the pin.

16. The solder pre-form of claim 5 wherein the solder pre-form comprises tin, gold, or indium.

* * * * *